United States Patent
Tian

(10) Patent No.: US 9,804,131 B2
(45) Date of Patent: Oct. 31, 2017

(54) ELECTROMAGNETIC ULTRASONIC TRANSDUCER AND ON-LINE INSPECTION SYSTEM COMPRISING SAME

(71) Applicants: Zhiheng Tian, Hunan (CN); Li Tian, Hunan (CN); Lu Tian, Hunan (CN)

(72) Inventor: Zhiheng Tian, Hunan (CN)

(73) Assignees: Zhiheng Tian, Hunan (CN); Li Tian, Hunan (CN); Lu Tian, Hunan (CN)

( * ) Notice: Subject to any disclaimer, the term of this patent is extended or adjusted under 35 U.S.C. 154(b) by 251 days.

(21) Appl. No.: 14/427,002

(22) PCT Filed: Sep. 12, 2013

(86) PCT No.: PCT/CN2013/083364
§ 371 (c)(1),
(2) Date: Mar. 10, 2015

(87) PCT Pub. No.: WO2014/040543
PCT Pub. Date: Mar. 20, 2014

(65) Prior Publication Data
US 2015/0241394 A1 Aug. 27, 2015

(30) Foreign Application Priority Data
Sep. 12, 2012 (CN) .......................... 2012 1 0336898

(51) Int. Cl.
*G01N 9/24* (2006.01)
*G01N 29/22* (2006.01)
(Continued)

(52) U.S. Cl.
CPC ........... *G01N 29/22* (2013.01); *G01N 29/225* (2013.01); *G01N 29/2412* (2013.01);
(Continued)

(58) Field of Classification Search
CPC .... G01N 29/22; G01N 29/36; G01N 29/4445; G01N 2291/101; G01N 29/225;
(Continued)

(56) References Cited

U.S. PATENT DOCUMENTS 4,373,199 A * 2/1983 Watanabe ............ G11B 3/0952
369/65
4,975,623 A * 12/1990 Iketani .................. H01H 51/34
181/192
(Continued)

FOREIGN PATENT DOCUMENTS

| CN | 201181290 Y | 1/2009 |
| CN | 201796015 U | 4/2011 |

(Continued)

OTHER PUBLICATIONS

Tan et al. (English Translation of Chinese Patent Application Publication CN 201796015 (U)).*
(Continued)

*Primary Examiner* — Laura Martin
*Assistant Examiner* — Samir M Shah
(74) *Attorney, Agent, or Firm* — Marshall, Gerstein & Borun LLP

(57) ABSTRACT

The electromagnetic ultrasonic transducer includes a detection bottom surface and a stopper connected to a sidewall of the electromagnetic ultrasonic transducer; wherein the stopper extends towards the detection bottom surface; a bottom surface of the stopper is lower than the detection bottom surface; a distance "d" between the bottom surface of the stopper and the detection bottom surface is in a range 0 mm<d≤1 mm; the bottom surface of the stopper contacts a surface of an object to be detected in a working state of the electromagnetic ultrasonic transducer.

5 Claims, 3 Drawing Sheets

(51) Int. Cl.
  *G01N 29/24* (2006.01)
  *G01N 29/265* (2006.01)
  *G01N 29/36* (2006.01)
  *G01N 29/44* (2006.01)

(52) U.S. Cl.
  CPC ........... *G01N 29/265* (2013.01); *G01N 29/36* (2013.01); *G01N 29/4445* (2013.01); *G01N 2291/044* (2013.01); *G01N 2291/101* (2013.01)

(58) Field of Classification Search
  CPC ........... G01N 29/2412; G01N 29/2406; G01N 29/24; G01N 29/26; G01N 2291/0234
  USPC .......................................................... 73/643
  See application file for complete search history.

(56) References Cited

U.S. PATENT DOCUMENTS

| | | | | |
|---|---|---|---|---|
| 6,108,432 | A * | 8/2000 | Watanabe | G10K 9/22 381/355 |
| 6,993,971 | B2 * | 2/2006 | Bossi | G01N 29/11 73/620 |
| 8,713,998 | B2 * | 5/2014 | Troy | B64F 5/0045 73/104 |
| 8,943,892 | B2 * | 2/2015 | Garvey | G01N 29/225 700/213 |
| 2001/0033224 | A1 * | 10/2001 | Togawa | G10K 9/22 340/384.1 |
| 2007/0074572 | A1 * | 4/2007 | Koch | B06B 1/04 73/627 |
| 2007/0222128 | A1 * | 9/2007 | Ichikawa | F16F 13/26 267/140.14 |
| 2010/0095775 | A1 * | 4/2010 | Sarr | G01N 29/265 73/621 |
| 2012/0200021 | A1 * | 8/2012 | Kanaya | F16F 13/268 267/140.14 |
| 2013/0221768 | A1 * | 8/2013 | Kawarai | H02K 35/02 310/30 |
| 2013/0304251 | A1 * | 11/2013 | Garvey | G01N 29/225 700/213 |

FOREIGN PATENT DOCUMENTS

| | | | | |
|---|---|---|---|---|
| CN | 102866205 A | | 1/2013 | |
| CN | 202886336 U | | 4/2013 | |
| JP | 53-057089 | | 5/1978 | |
| JP | 54-8585 | | 1/1979 | |
| JP | 9-280969 | | 10/1997 | |
| JP | 9-281089 | | 10/1997 | |
| JP | WO 2009057348 A1 | * | 5/2009 | ............. H02K 35/02 |
| JP | 3163956 U | * | 11/2010 | ............. H02K 35/02 |
| RU | 2298180 C2 | | 4/2007 | |
| RU | 2390014 C1 | | 5/2010 | |
| WO | WO-2007013836 A1 | | 2/2007 | |

OTHER PUBLICATIONS

Search Report in International Application No. PCT/CN2013/083364 dated Dec. 12, 2013.

* cited by examiner

ELECTROMAGNETIC ULTRASONIC TRANSDUCER AND ON-LINE INSPECTION SYSTEM COMPRISING SAME

CROSS-REFERENCE TO RELATED APPLICATIONS

This is the U.S. national phase of International Application No. PCT/CN2013/083364 filed on Sep. 12, 2013, which claims priority to Chinese patent application No. 201210336898.0, filed on Sep. 12, 2012, the entire respective disclosures of which are incorporated herein by reference.

FIELD OF THE INVENTION

The present disclosure relates to the field of nondestructive inspection technology, and more particularly to an electromagnetic ultrasonic transducer and an on-line inspection system including the same.

BACKGROUND

In the field of nondestructive inspection, piezoelectric ultrasonic and electromagnetic ultrasonic are commonly used to detect defects such as delamination, shrinkage, holes, inclusions, bubble, inside crack of metal material such as steel plates, so as to meet growing market demands for high quality steel such as ship plate steel and high pressure vessel steel. Piezoelectric ultrasonic inspection devices are gradually replaced by electromagnetic ultrasonic inspection devices because the piezoelectric ultrasonic inspection devices have following problems in operation such as a narrow operating temperature range for detecting steel plate, consuming a large amount of coupling pure water or other coupling agent, susceptible to interference, resulting in a misjudgment. The electromagnetic ultrasonic inspection devices do not use coupling agent, and do not need to contact an object to be detected, and can directly detect a moving object or an object having a rough surface, rust and a paint layer, without interference, and have high detection accuracy.

RU2298180 discloses using a plurality of electromagnetic ultrasonic transducers to detect defects of steel plates on-line. Each electromagnetic ultrasonic transducer includes a separate cylinder, which moves vertically, to drive the electromagnetic ultrasonic transducer to move vertically. With such a structure, the electromagnetic ultrasonic transducers can be selected to operate or not operate, so as to satisfy different sizes of steel plates to be detected or different detection surfaces. WO2007/013836A1 discloses using compressed air to pass through an electromagnetic ultrasonic transducer to form an air cushion layer between the electromagnetic ultrasonic transducer and a steel plate to be detected. When the steel plate moves upward, a distance between the electromagnetic ultrasonic transducer and the steel plate is shortened, the air cushion layer is reduced, pressure is increased, and thus the electromagnetic ultrasonic transducer is driven to automatically move upward following the steel plate. When using such a structure, at a moment when the electromagnetic ultrasonic transducer moves to an operating position from a waiting position, the electromagnetic ultrasonic transducer easily collides with the steel plate, causing wearing of the detection surface. Further, the flow of the compressed air used to form the air cushion layer may be reduced because compressed air pipeline is partially blocked or other reasons, the pressure is not enough, and the electromagnetic ultrasonic transducer is not balanced which causes the electromagnetic ultrasonic transducer to contact the steel plate and wear the detection surface. In addition, the above system requires a large air supply system, and thus has a very complex structure.

SUMMARY

The present disclosure aims to provides an electromagnetic ultrasonic transducer and an on-line inspection system including the transducer, to solve the technical problem in the prior art that the detection bottom surface collides with the surface of the objected to be detected and thus worn.

In order to achieve the above object, according to one aspect of the present disclosure, an electromagnetic ultrasonic transducer is provided and includes a detection bottom surface and a stopper connected to a sidewall of the electromagnetic ultrasonic transducer; wherein the stopper extends towards the detection bottom surface; a bottom surface of the stopper is lower than the detection bottom surface; a distance "d" between the bottom surface of the stopper and the detection bottom surface is in a range 0 mm<d≤1 mm; the bottom surface of the stopper contacts a surface of an object to be detected in a working state of the electromagnetic ultrasonic transducer.

According to another aspect of the present disclosure, an on-line inspection system is provided and includes an on-line inspection system including an electromagnetic ultrasonic transducer, a lifting system configured to control lifting of the electromagnetic ultrasonic transducer, and a signal generation and processing system configured to control the electromagnetic ultrasonic transducer to perform an inspection operation; wherein the electromagnetic ultrasonic transducer includes: a detection bottom surface and a stopper connected to a sidewall of the electromagnetic ultrasonic transducer; the stopper extends towards the detection bottom surface; a bottom surface of the stopper is lower than the detection bottom surface; a distance "d" between the bottom surface of the stopper and the detection bottom surface is in a range 0 mm<d≤1 mm; the bottom surface of the stopper contacts a surface of an object to be detected in a working state of the electromagnetic acoustic transducer.

In the electromagnetic ultrasonic transducer and the on-line inspection system including the electromagnetic ultrasonic transducer of the present disclosure, the stopper is connected to the sidewall of the electromagnetic ultrasonic transducer and extends towards the detection bottom surface, and the bottom surface of the stopper is lower than the detection bottom surface. With such structure, when the electromagnetic ultrasonic transducer moves downward to a surface of the object to be detected, the bottom surface of the stopper contacts the surface of the object to be detected and is supported by the object to be detected, so as to limit the distance between the detection bottom surface of the electromagnetic ultrasonic transducer and the object to be detected, thereby ensuring a detection signal to noise ratio of the electromagnetic ultrasonic transducer, improving inspection accuracy, also preventing the detection bottom surface of the electromagnetic ultrasonic transducer from colliding with the surface of the objected to be detected and preventing damage of the detection bottom surface caused by collision.

BRIEF DESCRIPTION OF THE DRAWINGS

Accompanying drawings constituting a part of the present application are provided for understanding of the present disclosure. Exemplary embodiments and descriptions of the exemplary embodiments of the present disclosure are intended to explain but not to limit the present disclosure. In the accompanying drawings:

FIG. 2b is a schematic diagram illustrating structures within an area indicated by A of FIG. 2a.

DETAILED DESCRIPTION

The present disclosure is described in detail hereinafter with reference to the accompanying drawings and embodiments. It should be noted, in case of no conflict, the embodiments of the present application and features of the embodiments can be combined with each.

Figure 1:
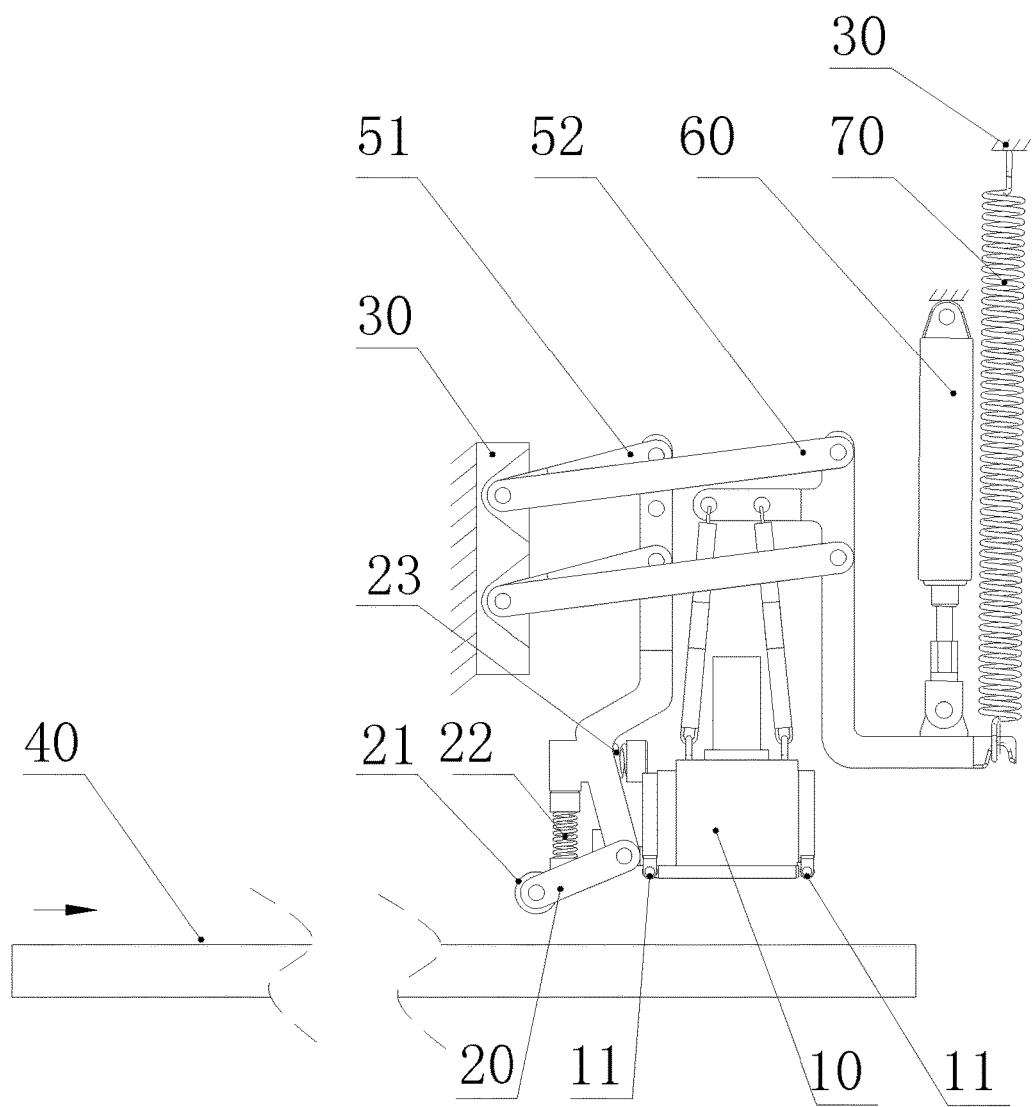
FIG. 1 is a partial structure diagram schematically illustrating an on-line inspection system in a non-working state according to one embodiment of the present disclosure.
Figure 2A:
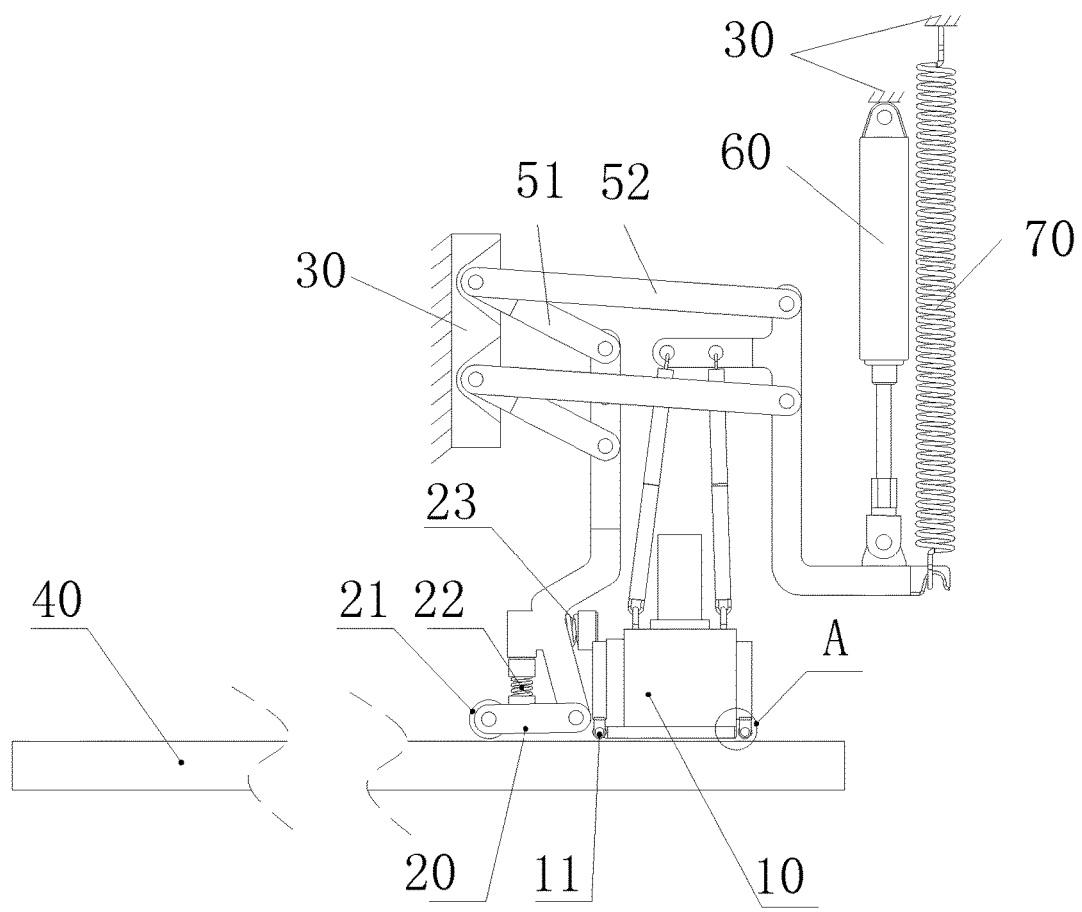
FIG. 2a is a partial structure diagram schematically illustrating an on-line inspection system of FIG. 1 in a working state.
Figure 2B:
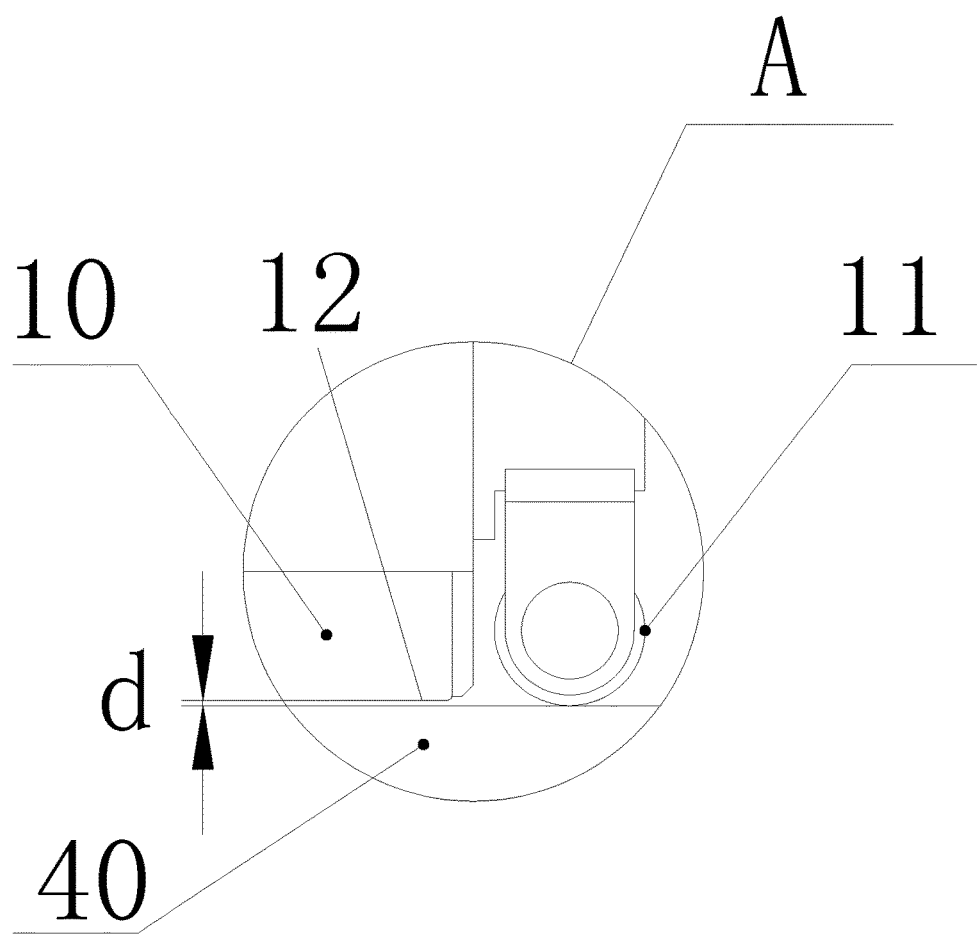

As shown in FIGS. 1-2b, an electromagnetic ultrasonic transducer 10 according to one embodiment of the present disclosure has a detection bottom surface 12. A stopper 11 is connected to a sidewall of the electromagnetic ultrasonic transducer 10. The stopper 11 extends towards the detection bottom surface 12. A bottom surface of the stopper 11 is lower than the detection bottom surface 12. The bottom surface of the stopper 11 has a smooth surface to reduce the wear on an object to be detected. The bottom surface of the stopper 11 is lower than the detection bottom surface 12 by a distance d, and 0 mm<d≤mm, preferably, 0.2 mm≤d≤0.6 mm. One stopper 11 is provided on each sidewall of the electromagnetic ultrasonic transducer 10. Alternatively, a pair of stoppers 11 are provided on any two opposite sidewalls. A distance between the stoppers 11 in a movement direction of the objected to be detected 40 is less than a minimum bending radius of the objected to be detected 40, to prevent the object to be detected 40 from scratching the detection bottom surface 12 when the objected to be detected 40 is uneven, thereby preventing damage of the electromagnetic ultrasonic transducer 10. The stopper 11 includes a tracking wheel. A bottom surface of the tracking wheel is the bottom surface of the stopper 11. A rotation central axis of the tracking wheel is arranged to be parallel to the detection bottom surface 12. The objected to be detected 40 is metal.

In the electromagnetic ultrasonic transducer 10 according to one embodiment of the present disclosure, the stopper 11 is connected to the sidewall of the electromagnetic ultrasonic transducer 10 and extends towards the detection bottom surface 12, and the bottom surface of the stopper 11 is lower than the detection bottom surface 12. With such structure, when the electromagnetic ultrasonic transducer 10 moves downward to a surface of the object to be detected 40, the bottom surface of the stopper 11 contacts the surface of the object to be detected 40 and is supported by the object to be detected 40, so as to limit a distance between the detection bottom surface 12 of the electromagnetic ultrasonic transducer 10 and the object to be detected 40, thereby ensuring a detection signal to noise ratio of the electromagnetic ultrasonic transducer 10, improving flaw detection accuracy, also preventing the detection bottom surface 12 of the electromagnetic ultrasonic transducer 10 from colliding with the surface of the objected to be detected 40 and preventing damage of the detection bottom surface 12 caused by collision.

One embodiment of the present disclosure further provides an on-line inspection system, which includes an electromagnetic ultrasonic transducer 10, a lifting system configured to control lifting of the electromagnetic ultrasonic transducer 10, and a signal generation and processing system configured to control the electromagnetic ultrasonic transducer 10 to perform inspection operations. The electromagnetic ultrasonic transducer 10 is the electromagnetic ultrasonic transducer 10 described above.

In one embodiment, the lifting system includes a frame 30, a lifting system connection component 52 hinged to the frame 30, a driving device 60 having one end connected with the lifting system connection component 52 and another end fixed on the frame 30, and chains connecting the electromagnetic ultrasonic transducer 10 with the lifting system connection component 52. The driving device 60 is a cylinder 60. Lower ends of two chains are hinged to a top end surface of the electromagnetic ultrasonic transducer 10. One sidewall of the electromagnetic ultrasonic transducer 10 away from the cylinder 60 is hinged to a lower end of a buffer arm connection component 51. A balance elastic member 70 such as a spring is provided between the frame 30 and the electromagnetic ultrasonic transducer 10, and is parallel to a driving direction of the driving device 60.

In the on-line inspection system, when the cylinder 60 is in an initial state, the chains are in a state of being tightened so as to bear weight of the electromagnetic ultrasonic transducer 10. When detection work is to be performed, the cylinder 60 is started, a piston of the cylinder 60 is elongated to push a piston connection member to move downward. As the same time, the electromagnetic ultrasonic transducer 10 moves downward toward the object to be detected 40 under action of the gravity of the electromagnetic ultrasonic transducer 10. When the electromagnetic ultrasonic transducer 10 falls on the object to be detected 40, the tracking wheels contact the surface of the object to be detected 40 so as to prevent the detection bottom surface 12 from colliding with the objected to be detected 40 and prevent damage of the detection bottom surface 12 caused by collision.

In order to further protect the detection bottom surface 12 of the electromagnetic ultrasonic transducer 10, the electromagnetic ultrasonic transducer 10 of one embodiment further includes a buffer device. The buffer device includes a buffer arm 20, a scroll wheel 21, a first elastic buffer member 22 and a buffer arm connection component 51 for connecting the buffer arm 20. One end of the buffer arm 20 is hinged to one sidewall of the electromagnetic ultrasonic transducer 10 and the scroll wheel 21, which is in a scrollable state and disposed on another end of the buffer arm 20. A bottom surface of the scroll wheel 21 is lower than a bottom surface of the buffer arm 20. A rotation central axis of the scroll wheel 21 is parallel to the sidewall to which the buffer arm 20 is hinged of the electromagnetic ultrasonic transducer 10. The first elastic buffer member 22 is connected between the buffer arm 20 and the buffer arm connection component 51. During rotation of the buffer arm 20, the first elastic buffer member 22 applies a downward force to the buffer arm 20. The first elastic buffer member 22 is vertically disposed. In a non-working state of the electromagnetic ultrasonic transducer 10, the bottom surface of the scroll wheel 21 is lower than the bottom surface of the stopper 11. In a working state of the electromagnetic ultrasonic transducer 10, a position of the bottom surface of the scroll wheel 21 is level with the bottom surface of the stopper 11. The buffer arm 20 includes a first section and a second section opposite to the first section. Relative ends of the first section and the second section are hinged to the sidewall of the electromagnetic ultrasonic transducer 10, respectively. A third section is connected between another two ends of the first section and the second section, and is parallel to the sidewall of the electromagnetic ultrasonic transducer 10. The scroll wheel 21 is pivoted to the third section. The first elastic buffer member 22 is a spring.

When adopting the on-line inspection system of this embodiment, the objected to be detected 40 moves at a certain speed, the cylinder 60 is started, the electromagnetic ultrasonic transducer 10 moves in a direction towards the objected to be detected 40 and drives the buffer arm connection component 51, the buffer arm 20 and the scroll wheel 21 to move together. Since when the electromagnetic ultrasonic transducer 10 is in the non-working state, a position of one end of the buffer arm 20 away from the electromagnetic ultrasonic transducer 10 is lower than the detection bottom surface 12 and the bottom surface of the scroll wheel 21 is lower than the bottom surface of the buffer arm 20, thus, when moving downward, the scroll wheel 21 first contacts the surface of the object to be detected 40 and drives the buffer arm 20 to rotate in relative to the electromagnetic ultrasonic transducer 10 via hinged action between the buffer arm 20 and the electromagnetic ultrasonic transducer 10, and then the buffer arm 20 moves on the surface of the object to be detected 40 until the bottom surface of the stopper 11 contacts the surface of the objected to be detected 40, thereby reducing impact force of the electromagnetic ultrasonic transducer 10 which moves downward, extending serving life of the tracking wheel and further preventing collision of the detection bottom surface 12. When moving on the surface of the object to be detected 40, the buffer arm 20 squeezes the first elastic buffer member 22, the elastic function of the first elastic buffer member 22 reduces a relative rotation speed between the buffer arm 20 and the electromagnetic ultrasonic transducer 10 and further reduces a speed at which the electromagnetic ultrasonic transducer 10 moves downward. After completion of the detection, when the cylinder 60 drives the electromagnetic ultrasonic transducer 10 to move upward, the buffer arm 20 is driven to rotate under action of the first elastic buffer member 22, and the end of the buffer arm 20 moves to below the detection bottom surface 12 to return to the initial state.

In order to prevent the electromagnetic ultrasonic transducer 10 from rotating along with an axis through which the electromagnetic ultrasonic transducer 10 is hinged to the buffer arm connection component 51 when all the tracking wheels of the electromagnetic ultrasonic transducer 10 contact the object to be detected 40, and to ensure that the bottom of the electromagnetic ultrasonic transducer 10 is parallel to the object to be detected 40. A horizontally disposed second elastic buffer member 23 such as a spring is connected between an end of the sidewall, away from the detection bottom surface 12, of the electromagnetic ultrasonic transducer 10, and a lateral side of one side of the buffer arm connection component 51 close to the electromagnetic ultrasonic transducer 10.

It can be seen from the above description, in the electromagnetic ultrasonic transducer 10 and the on-line inspection system including the electromagnetic ultrasonic transducer 10 of the present disclosure, the stopper 11 is connected to the sidewall of the electromagnetic ultrasonic transducer 10 and extends towards the detection bottom surface 12, and the bottom surface of the stopper 11 is lower than the detection bottom surface 12. With such structure, when the electromagnetic ultrasonic transducer 10 moves downward to the surface of the object to be detected 40, the bottom surface of the stopper 11 contacts the surface of the object to be detected 40 and is supported by the object to be detected 40, so as to prevent the detection bottom surface 12 of the electromagnetic ultrasonic transducer 10 from colliding with the surface of the objected to be detected 40 and prevent damage of the detection bottom surface 12 caused by collision.

Those described above are merely preferred embodiments of the present disclosure, but shall not be used to limit the present disclosure. For those skilled in the art, some modifications and alterations may be made without departing from the basic concept and the scope of the present disclosure, and these should fall within the scope of the present disclosure.

What is claimed is:

1. An on-line inspection system comprising:
an electromagnetic ultrasonic transducer;
a lifting system configured to control lifting of the electromagnetic ultrasonic transducer; and
a signal generation and processing system configured to control the electromagnetic ultrasonic transducer to perform an inspection operation;
wherein the electromagnetic ultrasonic transducer comprises: a detection bottom surface and a stopper connected to a sidewall of the electromagnetic ultrasonic transducer;
the stopper extends towards the detection bottom surface;
a bottom surface of the stopper is lower than the detection bottom surface;
a distance "d" between the bottom surface of the stopper and the detection bottom surface is in a range $0\ mm < d \leq 1\ mm$;
the bottom surface of the stopper contacts a surface of an object to be detected in a working state of the electromagnetic ultrasonic transducer;
the on-line inspection system further comprises: a buffer device;
wherein the buffer device comprises: a buffer arm, a scroll wheel, a first elastic buffer member and a buffer arm connection component;
one end of the buffer arm is hinged to one sidewall of the electromagnetic ultrasonic transducer;
the scroll wheel, in a scrollable state, is disposed on another end of the buffer arm;
a bottom surface of the scroll wheel is lower than a bottom surface of the buffer arm;
a rotation central axis of the scroll wheel is parallel to the sidewall of the electromagnetic ultrasonic transducer on which the buffer arm is hinged with the electromagnetic ultrasonic transducer;
the first elastic buffer member is connected between the buffer arm and the buffer arm connection component to assist in the movement of the buffer arm; and
the bottom surface of the scroll wheel has a state in which the bottom surface of the scroll wheel is lower than the bottom surface of the stopper in a non-working state of the electromagnetic ultrasonic transducer, and a state in which the bottom surface of the scroll wheel is level with the bottom surface of the stopper in a working state of the electromagnetic ultrasonic transducer.

2. The on-line inspection system according to claim 1, wherein the lifting system comprises: a frame;
a lifting system connection component hinged to the frame;
a driving device having one end connected with the lifting system connection component and another end fixed on the frame; and chains connecting the electromagnetic ultrasonic transducer with the lifting system connection component;

wherein the driving device drives the electromagnetic ultrasonic transducer to move upward or downward.

3. The on-line inspection system according to claim 2, further comprising a balance elastic member provided between the frame and the electromagnetic ultrasonic transducer and parallel to a driving direction of the driving device.

4. The on-line inspection system according to claim 1, wherein a horizontally disposed second elastic buffer member is connected between an end of the sidewall, away from the detection bottom surface, of the electromagnetic ultrasonic transducer, and a lateral side of one side of the buffer arm connection component close to the electromagnetic ultrasonic transducer.

5. The on-line inspection system according to claim 4, wherein the first elastic buffer member or the second elastic buffer member is a spring.

* * * * *